United States Patent [19]

Shimasaki et al.

[11] Patent Number: 5,700,946
[45] Date of Patent: Dec. 23, 1997

US005700946A

[54] PROCESS FOR PRODUCTION OF N-VINYL COMPOUND

[75] Inventors: Yuuji Shimasaki, Otsu; Hideyuki Kanbe, Izumiotsu; Akira Kurusu, Kyoto, all of Japan

[73] Assignee: Nippon Shokubai Co., Ltd., Osaka, Japan

[21] Appl. No.: 633,469

[22] Filed: Apr. 17, 1996

[30] Foreign Application Priority Data

Apr. 18, 1995 [JP] Japan .................................. 7-092759

[51] Int. Cl.$^6$ ................................................ C07D 263/04
[52] U.S. Cl. .......................... 548/231; 548/552; 560/157; 564/215
[58] Field of Search .......................... 548/552, 231; 564/215; 560/157

[56] References Cited

U.S. PATENT DOCUMENTS

| | | | |
|---|---|---|---|
| 2,592,254 | 4/1952 | Dickey | 260/77.5 |
| 2,905,690 | 9/1959 | Bakke | 260/307 |
| 3,019,231 | 1/1962 | Peppel et al. | 260/307 |
| 3,033,829 | 5/1962 | Bakke | 260/77.5 |
| 3,336,369 | 8/1967 | Schwiersch et al. | 260/482 |
| 3,346,586 | 10/1967 | Ingleby | 260/307 |
| 4,322,271 | 3/1982 | Jensen et al. | 204/73 |
| 4,511,722 | 4/1985 | Krimm et al. | 548/231 |
| 4,574,159 | 3/1986 | Hassdenteufel | 560/157 |
| 4,831,153 | 5/1989 | Phung | 548/231 |
| 5,059,713 | 10/1991 | Armor et al. | 564/187 |
| 5,233,077 | 8/1993 | Waller | 560/157 |
| 5,410,070 | 4/1995 | Franz et al. | 548/552 |

FOREIGN PATENT DOCUMENTS

| | | |
|---|---|---|
| 50-2969 | 1/1975 | Japan . |
| 1-199939 | 8/1989 | Japan . |
| 6256306 | 9/1994 | Japan . |
| 7-49398 | 5/1995 | Japan . |

OTHER PUBLICATIONS

Furukawa, et al. "Reaction of Vinyl Ethers with ...", J. Org. Chem., 23, 672–675 (1958).
Akashi, et al, "A Novel Synthetic Procedure ...", J. Polm. Sci: Part A: Poly. Chem. 28, 3487–3497 (1990).
Stackman, et al., "Synthesis of N–Vinylacetamide ...", Ind. Eng. Chem. Prod. Res. Dev. 1985, 24, 242–246.
Kutner, A., "Preparation, Properties and ..." J. Org. Chem., 26, 3495–3497 (1961).
Drechsel, E.K., "N–Vinyl–2–oxazolidone", J. Org. Chem., 22 849–851 (1957).
Zhang, et al, "Synthesis of N–vinyl–N–methylcarbamic ...", Huaxue Shijie 1987, 28(1), 10–13 (CA 106:157261 r).

Primary Examiner—Matthew V. Grumbling
Assistant Examiner—Michael Bucknum
Attorney, Agent, or Firm—Sherman and Shalloway

[57] ABSTRACT

The present invention provides a process for producing an N-vinyl compound, which comprises subjecting an N-(-alkoxyalkyl) compound to gas phase intramolecular alcohol elimination to convert said compound to an N-vinyl compound directly in one step, wherein a solid oxide containing phosphorus and an alkali metal and/or an alkaline earth metal is used as a catalyst. This process need not use any solvent or any auxiliary raw material and consequently can produce an N-vinyl compound simply and safely without generating any waste material derived from the auxiliary raw material.

4 Claims, No Drawings

PROCESS FOR PRODUCTION OF N-VINYL COMPOUND

The present invention relates to a process for producing an N-vinyl compound by subjecting an N-(1-alkoxyalkyl) compound to alcohol elimination in a gas phase.

N-vinyl compounds, when homopolymerized or copolymerized with other monomers, provide various functional polymers which are useful in the fields of complexing agent, adhesive, textile modifier, dyeing assistant, resin additive, flocculant, etc.

As to the production of N-vinyl compound by alcohol elimination from N-(1-alkoxyalkyl) compound, various processes such as exemplified below are known.

U.S. Pat. No. 3,336,369 discloses a process which comprises pyrolyzing an alkyl N-($\alpha$-alkoxyethyl)carbamate or an alkyl N-($\alpha$-alkoxyethyl)-N-alkylcarbamate in a liquid phase using, as a catalyst, acid aluminum oxide, acid aluminum phosphate or potassium sulfate-aluminum. In this process, however, the yield is insufficient in industrial application and is particularly low when an alkyl N-($\alpha$-alkoxyethyl)carbamate is used as the raw material.

U.S. Pat. No. 4,574,159 discloses a process which comprises pyrolyzing N-$\alpha$-methoxyethyl-O-methyl-urethane in a gas phase and cooling the reaction mixture to give rise to crystallization to obtain O-methyl-N-vinylurethane in a high purity. The literature, however, makes no mention of any catalyst for pyrolysis, or gives no specific description on details of reaction (e.g. size of reaction tube and space velocity). The present inventors conducted the gas-phase pyrolysis of the above process by filling glass beads (a heat conductor) in a stainless steel-made reaction tube (see Comparative Example 2 shown later); however, the conversion of the raw material was very low as compared with when the catalyst of the present invention was used. That is, in the above process, it was impossible to produce O-methyl-N-vinylurethane in an industrially acceptable yield without using any catalyst for pyrolysis.

U.S. Pat. No. 4,831,153 proposes a process which comprises pyrolyzing an N-(1-hydroxyalkyl)-2-oxazolidone or an N-(1-hydroxycarbyloxyalkyl)-2-oxazolidone in a gas phase to produce an N-vinyl-2-oxazolidone. This process uses, as a catalyst, a weak acid or a weakly acidic metal salt, preferably $H_3BO_4$, $Na_2SO_4$, $K_2SO_4$, $CuSO_4$ or the like. In the process, however, the yield of intended N-vinyl-2-oxazolidone is not sufficient and no study is made on the life of the catalyst; therefore, the process cannot be regarded as an industrially applicable technique.

Japanese Patent Application Kokai (Laid-Open) No. 256306/1994 discloses a process which comprises reacting an N-alkylpyrrolidone on an acidic non-homogeneous catalyst other than oxides of metals of group IIb, group IIIb, group IVb and group VIb to produce an N-alkenylpyrrolidone. The literature, however, merely provides a technique in which part of the catalyst elements used in the prior art are excluded, and gives no specific data demonstrating that all the compounds of elements not excluded are effective; therefore, the catalyst used in the process has too broad a definition and is ambiguous. While, as well known, two catalyst containing the same element, generally show largely different performances when they have different compositions, different calcination temperatures, etc., the literature mention, as specific examples of the catalyst used in the Process, only two catalysts [$H_3PO_4$ and $La(H_2PO_4)_3$]. Further, the literature neither includes any Example of reacting an N-(1-alkoxyalkyl) compound, nor even suggests any catalyst which is useful in production of N-vinyl compound by alcohol elimination from N-(1-alkoxyalkyl) compound.

Japanese Patent Publication No. 49398/1995 discloses a process which comprises heating a carboxylic acid amide having an eliminatable group at the $\alpha$-position, in the presence of a porous catalyst comprising MgS, calcium oxide, strontium oxide or a mixture of the two oxides, to produce an N-vinylamide.

J. Org. Chem., Vol. 23, 672–675, 1958 reports a process which comprises subjecting an N-(1-alkoxyalkyl)-succinimide to alcohol elimination to produce an N-vinylsuccinimide.

U.S. Pat. No. 4,322,271 discloses a process which comprises subjecting an N-$\alpha$-alkoxyethyl-N-alkylcarboxylamide to alcohol elimination in the presence or absence of a catalyst to produce an N-vinyl-N-alkylcarboxylamide. In the literature, there are mentioned, as the catalyst, weakly acidic oxides of Al, Be, Zr or W; weakly acidic phosphates of Ca, Al, Mo, B and W; etc.

The object of the present invention is to provide an improved process for producing an N-vinyl compound from an N-(1-alkoxyalkyl) compound, wherein an N-(1-alkoxyalkyl) compound can be converted directly to an N-vinyl compound in a gas phase in one step at a high conversion at a high selectivity, without using any auxiliary raw material or any solvent.

The present inventors made an extensive study on a process capable of subjecting an N-(1-alkoxyalkyl) compound to alcohol elimination in a gas phase in one step, as well as on a catalyst effectively used in the process. As a result, the present inventors found out that by using, as a catalyst, a solid oxide containing phosphorus and an alkali metal and/or an alkaline earth metal, an N-(1-alkoxyalkyl) compound can be converted to an N-vinyl compound at a high conversion at a high selectivity (such a high conversion and such a high selectivity have been unobtainable heretofore) stably over a long period of time. The finding has led to the completion of the present invention.

According to the present invention, there is provided a process for producing an N-vinyl compound, which comprises subjecting an N-(1-alkoxyalkyl) compound to gas phase intramolecular alcohol elimination to convert said compound to an N-vinyl compound directly in one step, wherein a solid oxide containing phosphorus and an alkali metal and/or an alkaline earth metal is used as a catalyst.

The present invention is hereinafter described in detail.

In the present process, gas phase intramolecular alcohol elimination from an N-(1-alkoxyalkyl) compound to an N-vinyl compound, represented by the following formula (14) is conducted in a gas phase in the presence of a novel catalyst:

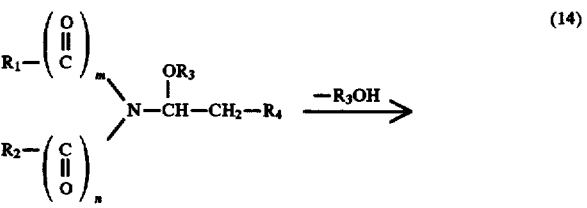

(14)

-continued

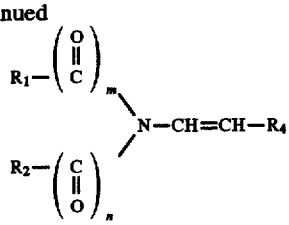

(wherein m and n are each independently 0 or 1 and $R_1$ and $R_2$ are each independently one member selected from the group consisting of hydrogen, hydrocarbon groups having 1–8 carbon atoms and alkoxy groups having 1–6 carbon atoms with provisos that, when m and n are each 0, none of $R_1$ and $R_2$ are hydrogen and, when none of $R_1$ and $R_2$ are hydrogen, $R_1$ and $R_2$ may bond to each other to form, together with. N, a five- to seven-membered ring which may contain unsaturated bond(s) and/or hetero atom(s) selected from the group consisting of S, O and N other than said N; $R_3$ is one member selected from the group consisting of methyl group, ethyl group, propyl group and butyl group; and $R_4$ is one member selected from the group consisting of hydrogen and hydrocarbon groups having 1–6 carbon atoms).

Preferable examples of the (N-1-alkoxyalkyl) compound used as a raw material in the present process are as follows:

an N-(1-alkoxyalkyl)-2-oxazolidone represented by the following general formula (3):

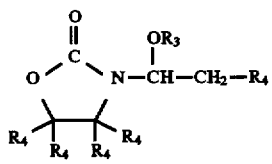

(3)

(wherein $R_3$ is one member selected from the group consisting of methyl group, ethyl group, propyl group and butyl group; and $R_4$ is one member selected from the group consisting of hydrogen, methyl group and ethyl group);

an N-(1-alkoxyalkyl)-O-alkylcarbamate represented by the following general formula (5):

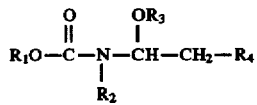

(5)

(wherein $R_1$ and $R_3$ are each independently one member selected from the group consisting of methyl group, ethyl group, propyl group and butyl group; $R_2$ is one member selected from the group consisting of hydrogen and hydrocarbon groups having 1–4 carbon atoms; and $R_4$ is one member selected from the group consisting of hydrogen, methyl group and ethyl group);

an N-(1-alkoxyalkyl)amide represented by the following general formula (7):

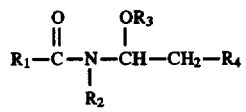

(7)

(wherein $R_1$ and $R_2$ are each independently one member selected from the group consisting of hydrogen and hydrocarbon groups having 1–8 carbon atoms with a proviso that $R_1$ and $R_2$ may bond to each other to form, together with N, a five- to seven-membered ring which may contain hetero atom(s) selected from the group consisting of S, O and N other than said N; $R_3$ is one member selected from the group consisting of methyl group, ethyl group, propyl group and butyl group; and $R_4$ is one member selected from the group consisting of hydrogen and hydrocarbon groups having 1–6 carbon atoms);

an N-(1-alkoxyalkyl)imide represented by the following general formula (9):

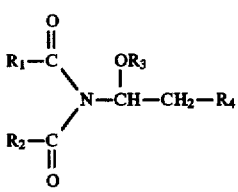

(9)

(wherein $R_1$ and $R_2$ are each independently one member selected from the group consisting of hydrogen and hydrocarbon groups having 1–8 carbon atoms with a proviso that $R_1$ and $R_2$ may bond to each other to form, together with N, a five- to seven-membered ring which may contain hetero atom(s) selected from the group consisting of S, O and N other than said N; $R_3$ is one member selected from the group consisting of methyl group, ethyl group, propyl group and butyl group; and $R_4$ is one member selected from hydrogen and hydrocarbon groups having 1–6 carbon atoms); and an N-(1-alkoxyalkyl)amine represented by the following general formula (11):

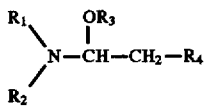

(11)

(wherein $R_1$ and $R_2$ are each independently one member selected from the group consisting of hydrocarbon groups having 1–8 carbon atoms with a proviso that $R_1$ and $R_2$ may bond to each other to form, together with N, a five- to seven-membered ring which may contain unsaturated bond (s) and/or hereto atom(s) selected from the group consisting of S, O and N other than said N; $R_3$ is one member selected from the group consisting of methyl group, ethyl group, propyl group and buryl group; and $R_4$ is one member selected from the group consisting of hydrogen and hydrocarbon groups having 1–6 carbon atoms). Needless to say, each of these N-(1-alkoxyalkyl) compounds should have such a vapor pressure that each compound can become a gas under the reaction conditions of the present invention.

The N-(1-alkoxyalkyl) compounds (3), (5), (7), (9) and (11) are converted, by the present process, to the following corresponding N-vinyl compounds, respectively:

an N-vinyl-2-oxazolidone represented by the following general formula (4):

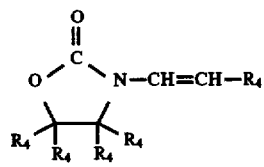

(4)

[wherein $R_4$ is the same as in the general formula (3)];

an N-vinyl-O-alkylcarbamate represented by the following general formula (6):

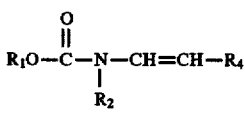

(6)

[wherein $R_1$, $R_2$ and $R_4$ are the same as in the general formula (5)];

an N-vinylamide represented by the following general formula (8):

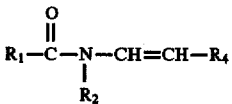

(8)

[wherein $R_1$, $R_2$ and $R_4$ are the same as in the general formula (7)];

an N-vinylimide represented by the following general formula (10):

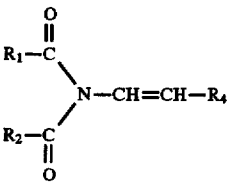

(10)

[wherein $R_1$, $R_2$ and $R_4$ are the same as in the general formula (9)]; and an N-vinylamine represented by the following general formula (12):

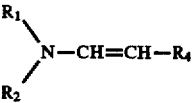

(12)

[wherein $R_1$, $R_2$ and $R_4$ are the same as in the general formula (11)].

Specific examples of the raw material preferably used in the present process are N-(1-alkoxyalkyl)-O-alkylcarbamates such as N-(1-methoxyethyl)-O-methylcarbamate, N-(1-ethoxyethyl)-O-methylcarbamate, N-(1-propoxyethyl)-O-methylcarbamate, N-(1-butoxyethyl)-O-methylcarbamate, N-(1-methoxypropyl)-O-methylcarbamate, N-(1-methoxybutyl)-O-methylcarbamate and the like; N-(1-alkoxyalkyl)-2-oxazolidones such as N-(1-methoxyethyl)-2-oxazolidone, N-(1-methoxyethyl)-5-methyl-2-oxazolidone, N-(1-methoxyethyl)-5-ethyl-2-oxazolidone, N-(1-ethoxyethyl)-2-oxazolidone, N-(1-propoxyethyl)-2-oxazolidone, N-(1-methoxypropyl)-2-oxazolidone, N-(1-methoxybutyl)-2-oxazolidone and the like; N-(1-alkoxyalkyl)amides such as N-(1-methoxyethyl) formaldehyde, N-(1-methoxyethyl)acetamide, N-(1-methoxyethyl)-N'-methylacetamide, N-(1-ethoxyethyl)-N'-methyl-acetamide and the like; N-(1-alkoxyalkyl)lactams such as N-(1-methoxyethyl)-2-pyrrolidone, N-(1-methoxyethyl)captolactam, N-(1-methoxyethyl)-2-morpholinone and the like; N-(1-alkoxyalkyl)imides such as N-(1-methoxyethyl)succinimide, N-(1-ethoxyethyl) succinimide and the like; and N-(1-alkoxyalkyl)amines such as N-(1-methoxyethyl)pyrrole, N-(1-methoxyethyl) imidazole and the like. Of course, the raw material is not restricted to these examples.

The catalyst of the present invention shows substantially no reduction in activity even when used in the present process continuously over a long period of time. The catalyst, even if its activity has been deteriorated owing to coking, etc., can recover its activity by passing air therethrough to burn the coke.

The catalyst used in the present process is a solid oxide containing phosphorus and an alkali metal and/or an alkaline earth metal. It is preferably a solid oxide represented by the following general formula (13):

(13)

(wherein P is phosphorus; X is at least one element selected from the group consisting of alkali metals and alkaline earth metals; Y is at least one element selected from the group consisting of Ti, Zr, Nb, B, Al and Si; O is oxygen; a, b and c are atomic ratios of P, X and Y, respectively with a proviso that when a=1, b is in the range of 0.5–5 and c is in the range of 0–500; and d is a figure determined by a, b, c and the bonding states of the individual components).

There is no particular restriction as to the method for preparation of the catalyst, and any known method can be used. As the source of phosphorus which is one essential component of the catalyst, there can be used phosphorus pentachloride, phosphoric acid, phosphoric acid salts, phosphoric acid esters, other organic phosphorus compounds, etc. As the sources of the alkali metal and/or alkaline earth metal which is other essential component, there can be used oxides, hydroxides, halides, salts (e.g. carbonates, nitrates, carboxylates, phosphates and sulfates), metals per se, etc.

Preferable examples of the method for preparation of the present catalyst include:

(1) a method which comprises molding phosphoric acid or a phosphoric acid salt and a source(s) of an alkali metal or (and) an alkaline earth metal in the presence of an appropriate molding aid (e.g. water or an alcohol), followed by drying and calcination;

(2) a method which comprises impregnating or mixing a non-essential catalyst element oxide with an aqueous solution containing phosphoric acid or a phosphoric acid salt and a source(s) of an alkali metal or (and) an alkaline earth metal, molding the resulting material, and drying and calcining the molded material;

(3) a method which comprises impregnating a molded material (e.g. spherical, columnar or ring-like) of a non-essential catalyst element oxide with an aqueous solution containing phosphoric acid or a phosphoric acid salt and a source(s) of an alkali metal or (and) an alkaline earth metal, and drying and calcining the impregnated molded material; and (4) a method which comprises dissolving or suspending, in water, a phosphorus source, a source(s) of an alkali metal or (and) an alkaline earth metal, and other catalyst element source, concentrating the solution or suspension with heating and stirring, and drying, molding and calcining the concentrate.

The calcination temperature of the catalyst can be in the broad range of 300°–1,000° C., preferably 400°–800° C. although it varies depending upon the kinds of the raw materials for catalyst.

The reactor used in carrying out the present process can be any of a fixed bed type and a fluidized bed type. The reaction is conducted at such a temperature and pressure that the raw material [N-(1-alkoxyalkyl) compound] can be kept in a gas phase. The reaction pressure is usually ordinary pressure or a reduced pressure, but may be an applied pressure. The appropriate reaction temperature is 150°–500° C., preferably 180°–450° C. although it varies depending upon other reaction conditions. When the reaction temperature is lower than 150° C., the conversion of the raw material [N-(1-alkoxyalkyl) compound] is significantly low. When the reaction temperature is higher than 500° C., the selectivity of intended N-vinyl compound is significantly low. The raw material [N-(1-alkoxyalkyl) compound] is diluted with a substance inert to the reaction, such as nitrogen, helium, argon, hydrocarbon or the like and/or placed under vacuum, whereby the raw material is allowed to have a partial pressure of preferably 5–600 mmHg; thereafter, the raw material is fed into the catalyst layer. The space velocity (GHSV) of the raw material [N-(1-alkoxyalkyl) compound] is ordinarily 1–1.000 h$^{-1}$ preferably 10–500 h$^{-1}$ although it varies depending upon other reaction conditions.

As stated above, according to the present process, an N-(1-alkoxyalkyl) compound can be converted to an N-vinyl compound directly in one step continuously without using any solvent or any auxiliary raw material. Therefore, the present process can produce an N-vinyl compound simply and safely without generating any waste material derived from the auxiliary raw material, and is very useful in industry.

The present invention is hereinafter described specifically by way of Examples. However, the present invention is not restricted to these Examples.

In the Examples, "conversion", "selectivity" and "per-pass yield" have the following definitions.

Conversion (mole %)=100×[moles of consumed N-(1-alkoxyalkyl) compound]/[moles of fed N-(1-alkoxyalkyl) compound]

Selectivity (mole %)=100×[moles of produced N-vinyl compound]/[moles of consumed N-(1-alkoxyalkyl) compound]

Per-pass yield (%)=100×[moles of produced N-vinyl compound]/[moles of fed N-(1-alkoxyalkyl) compound]

EXAMPLE 1

[Catalyst Preparation]

A solution of 13.2 g of diammonium hydrogenphosphate in 50 g of water was added to a solution of 4.2 g of lithium hydroxide monohydrate in 50 g of water. Thereto was added 30.0 g of silicon oxide. The mixture was heated with stirring, to vaporize water until the resulting residue became dry. The residue was dried in air at 120° C. for 20 hours, crushed into particles of 9–16 mesh, and calcined in air at 600° C. for 2 hours to prepare a catalyst having a composition of $P_1Li_1Si_5$ in terms of atomic ratio when oxygen was excluded.

[Reaction]

5 ml of the above catalyst was filled in a stainless steel-made reaction tube having an inside diameter of 10 min. The reaction tube was immersed in a molten salt bath of 270° C. Into the reaction tube was fed a raw material gas obtained by diluting N-(1-methoxyethyl)-2-oxazolidone with nitrogen so that the partial pressure of the N-(1-methoxyethyl)-2-oxazolidone became 76 mmHg, at a space velocity of N-(1-methoxyethyl)-2-oxazolidone, of 200 h$^{-1}$ to give rise to a reaction at ordinary pressure. The gas from the reaction tube outlet after 1 hour from the start of raw material feeding was collected into methanol and analyzed by gas chromatography. As a result, the conversion of N-(1-methoxyethyl)-2-oxazolidone was 99.0 mole %; and the selectivity and per-pass yield of N-vinyl-2-oxazolidone were 98.0 mole % and 97.0 mole %, respectively.

COMPARATIVE EXAMPLE 1

[Catalyst Preparation]

30.0 g of spherical silica gel of 5–10 mesh was dried in air at 120° C. for 20 hours and then calcined in air at 500° C. for 2 hours to prepare a catalyst.

[Reaction]

Using the above catalyst, a reaction was conducted in the same manner as in Example 1. After 1 hour from the start of raw material feeding, the conversion of N-(1-methoxyethyl)-2-oxazolidone was 69.0 mole %; and the selectivity and per-pass yield of N-vinyl-2-oxazolidone were 97.9 mole % and 67.6 mole %, respectively.

EXAMPLE 2

[Catalyst Preparation]

A catalyst having a composition of $P_1Na_1Si_5$ in terms of atomic ratio when oxygen was excluded, was prepared in the same manner as in Example 1 except that lithium hydroxide monohydrate was changed to 4.0 g of sodium hydroxide.

[Reaction]

Using the above catalyst, a reaction was conducted in the same manner as in Example 1. After 1 hour from the start of raw material feeding, the conversion of N-(1-methoxyethyl)-2-oxazolidone was 98.5 mole %; and the selectivity and per-pass yield of N-vinyl-2-oxazolidone were 97.8 mole % and 96.3 mole %, respectively.

EXAMPLE 3

[Catalyst Preparation]

A catalyst having a composition of $P_1K_1Si_5$ in terms of atomic ratio when oxygen was excluded, was prepared in the same manner as in Example 1 except that lithium hydroxide monohydrate was changed to 5.6 g of potassium hydroxide.

[Reaction]

Using the above catalyst, a reaction was conducted in the same manner as in Example 1. After 1 hour from the start of raw material feeding, the conversion of N-(1-methoxyethyl)-2-oxazolidone was 98.0 mole %; and the selectivity and per-pass yield of N-vinyl-2-oxazolidone were 98.9 mole % and 96.9 mole %, respectively.

EXAMPLE 4

[Catalyst Preparation]

A solution of 2.64 g of diammonium hydrogenphosphate in 30 g of water was added to a solution of 0.84 g of lithium hydroxide monohydrate in 30 g of water. Thereto was added 26.6 g of niobium pentoxide. The mixture was heated with stirring, to vaporize water until the resulting residue became dry. The residue was dried in air at 120° C. for 20 hours, crushed into particles of 9–16 mesh, and calcined in air at 500° C. for 2 hours to prepare a catalyst having a composition of $P_1Li_1Nb_{10}$ in terms of atomic ratio when oxygen was excluded.

[Reaction]

Using the above catalyst, a reaction was conducted in the same manner as in Example 1 except that the raw material for reaction was changed to N-(1-methoxyethyl)-5-methyl-2-oxazolidone. After 1 hour from the start of raw material feeding, the conversion of N-(1-methoxyethyl)-5-methyl-2-oxazolidone was 97.6 mole %; and the selectivity and per-pass yield of N-vinyl-5-methyl-2-oxazolidone were 98.7 mole % and 96.3 mole %, respectively.

EXAMPLE 5

[Catalyst Preparation]

A solution of 6.6 g of diammonium hydrogenphosphate in 50 g of water was added to a solution of 2.1 g of lithium hydroxide monohydrate in 50 g of water. Thereto was added 46.2 g of zirconium silicate. The mixture was heated with stirring, to vaporize water until the resulting residue became dry. The residue was dried in air at 120° C. for 20 hours, crushed into particles of 9–16 mesh, and calcined in air at 500° C. for 2 hours to prepare a catalyst having a composition of $P_1Li_1Zr_5Si_5$ in terms of atomic ratio when oxygen was excluded.

[Reaction]

Using the above catalyst, a reaction was conducted in the same manner as in Example 1 except that the raw material for reaction was changed to N-(1-propoxyethyl)-5-methyl-2-oxazolidone. After 1 hour from the start of raw material feeding, the conversion of N-(1-propoxyethyl)-5-methyl-2-oxazolidone was 97.3 mole %; and the selectivity and per-pass yield of N-vinyl-5-methyl-2-oxazolidone were 99.3 mole % and 96.6 mole %, respectively.

EXAMPLE 6

[Catalyst Preparation]

A solution of 15.6 g of sodium dihydrogenphosphate dihydrate in 50 g of water was added to 40.0 g of titanium dioxide. The mixture was heated with stirring, to vaporize water until the resulting residue became dry. The residue was dried in air at 120° C. for 20 hours, crushed into particles of 9–16 mesh, and calcined in air at 500° C.; for 2 hours to prepare a catalyst having a composition of $P_1Na_1Ti_5$ in terms of atomic ratio when oxygen was excluded.

[Reaction]

Using the above catalyst, a reaction was conducted in the same manner as in Example 1 except that the raw material for reaction was changed to N-(1-methoxyethyl)-5-ethyl-2-oxazolidone. After 1 hour from the start of raw material feeding, the conversion of N-(1-methoxyethyl)-5-ethyl-2-oxazolidone was 97.1 mole %; and the selectivity and per-pass yield of N-vinyl-5-ethyl-2-oxazolidone were 98.7 mole % and 95.8 mole %, respectively.

EXAMPLE 7

[Catalyst Preparation]

17.4 g of magnesium hydrogenphosphate trihydrate and 30.0 g of silicon oxide were kneaded with 50 g of water in a mortar. The mixture was dried in air at 120° C. for 20 hours, crushed into particles of 9–16 mesh, and calcined in air at 500° C. for 2 hours to prepare a catalyst having a composition of $P_1Mg_1Si_5$ in terms of atomic ratio when oxygen was excluded.

[Reaction]

Using the above catalyst, a reaction was conducted in the same manner as in Example 1 except that the reaction temperature was changed to 250° C., the partial pressure of raw material was changed to 38 mmHg and the space velocity of raw material was changed to 100 $h^{-1}$. After 1 hour from the start of raw material feeding, the conversion of N-(1-methoxyethyl)-2-oxazolidone was 93.1 mole %; and the selectivity and per-pass yield of N-vinyl-2-oxazolidone were 98.2 mole % and 91.4 mole %, respectively.

EXAMPLE 8

[Catalyst preparation]

A catalyst having a composition of $P_1Ca_1Si_5$ in terms of atomic ratio when oxygen was excluded, was prepared in the same manner as in Example 7 except that magnesium hydrogenphosphate trihydrate was changed to 17.2 g of calcium hydrogenphosphate dihydrate.

[Reaction]

Using the above catalyst, a reaction was conducted in the same manner as in Example 1 except that the reaction temperature was changed to 250° C., the partial pressure of raw material was changed to 38 mmHg and the space velocity of raw material was changed to 100 $h^{-1}$. After 1 hour from the start of raw material feeding, the conversion of N-(1-methoxyethyl)-2-oxazolidone was 92.9 mole %; and the selectivity and per-pass yield of N-vinyl-2-oxazolidone were 98.6 mole % and 91.6 mole %, respectively.

EXAMPLE 9

[Catalyst Preparation]

A catalyst having a composition of $P_1Ba_1Si_5$ in terms of atomic ratio when oxygen was excluded, was prepared in the same manner as in Example 7 except that magnesium hydrogenphosphate trihydrate was changed to 3.3 g of barium hydrogenphosphate.

[Reaction]

Using the above catalyst, a reaction was conducted in the same manner as in Example 1 except that the reaction temperature was changed to 200° C., the partial pressure of raw material was changed to 38 mmHg and the space velocity of raw material was changed to 100 $h^{-1}$. After 1 hour from the start of raw material feeding, the conversion of N-(1-methoxyethyl)-2-oxazolidone was 96.7 mole %; and the selectivity and per-pass yield of N-vinyl-2-oxazolidone were 96.6 mole % and 93.4 mole %, respectively.

EXAMPLE 10

[Catalyst Preparation]

A solution of 13.2 g of diammonium hydrogenphosphate in 40 g of water was added to a solution of 5.2 g of lithium hydroxide monohydrate in 50 g of water. Thereto was added 30.0 g of silicon oxide. The mixture was heated with stirring, to vaporize water until the resulting residue became dry. The residue was dried in air at 120° C. for 20 hours, crushed into particles of 9–16 mesh, and calcined in air at 700° C. for 2 hours to prepare a catalyst having a composition of $P_1Li_{1.25}Si_5$ in terms of atomic ratio when oxygen was excluded.

[Reaction]

Using the above catalyst, a reaction was conducted in the same manner as in Example 1. After 1 hour from the start of raw material feeding, the conversion of N-(1-methoxyethyl)-2-oxazolidone was 99.5 mole %; and the selectivity and per-pass yield of N-vinyl-2-oxazolidone were 99.5 mole % and 99.0 mole %, respectively.

EXAMPLE 11

[Catalyst Preparation]

A solution of 13.2 g of diammonium hydrogenphosphate in 40 g of water was added to a solution of 8.4 g of lithium hydroxide monohydrate in 100 g of water. Thereto was added 30.0 g of silicon oxide. The mixture was heated with stirring, to vaporize water until the resulting residue became dry. The residue was dried in air at 120° C. for 20 hours, crushed into particles of 9–16 mesh, and calcined in air at 700° C. for 2 hours to prepare a catalyst having a composition of $P_1Li_2Si_5$ in terms of atomic ratio when oxygen was excluded.

[Reaction]

Using the above catalyst, a reaction was conducted in the same manner as in Example 1 except that the reaction temperature was changed to 300° C. After 1 hour from the start of raw material feeding, the conversion of N-(1-methoxyethyl)-2-oxazolidone was 99.1 mole %; and the selectivity and per-pass yield of N-vinyl-2-oxazolidone were 97.8 mole % and 96.9 mole %, respectively.

EXAMPLE 12

[Catalyst Preparation]

A solution of 57.6 g of a 85% aqueous phosphoric acid solution, in 200 g of water was added to a solution of 21.0 g of lithium hydroxide monohydrate and 7.8 g of aluminum hydroxide in 200 g of water. Thereto was added 12.0 g of silicon oxide. The mixture was heated with stirring, to vaporize water until the resulting residue became dry. The residue was dried in air at 120° C. for 20 hours, crushed into particles of 9–16 mesh, and calcined in air at 500° C. for 2 hours to prepare a catalyst having a composition of $P_1Li_1Al_{0.2}Si_{0.4}$ in terms of atomic ratio when oxygen was excluded.

[Reaction]

Using the above catalyst, a reaction was conducted in the same manner as in Example 1 except that the reaction temperature was changed to 250° C. After 1 hour from the start of raw material feeding, the conversion of N-(1-methoxyethyl)-2-oxazolidone was 95.9 mole %; and the selectivity and per-pass yield of N-vinyl-2-oxazolidone were 98.6 mole % and 94.6 mole %, respectively.

EXAMPLE 13

[Catalyst Preparation]

A solution of 57.6 g of a 85% aqueous phosphoric acid solution, in 200 g of water was added to a suspension of 21.0 g of lithium hydroxide monohydrate and 14.5 g of magnesium hydroxide in 200 g of water. The mixture was heated with stirring, to vaporize water until the resulting residue became dry. The residue was dried in air at 120° C. for 20 hours, crushed into particles of 9–16 mesh, and calcined in air at 500° C. for 2 hours to prepare a catalyst having a composition of $P_1Li_1Mg_{0.5}$ in terms of atomic ratio when oxygen was excluded.

[Reaction]

Using the above catalyst, a reaction was conducted in the same manner as in Example 1 except that the reaction temperature was changed to 250° C. After 1 hour from the start of raw material feeding, the conversion of N-(1-methoxyethyl)-2-oxazolidone was 90.1 mole %; and the selectivity and per-pass yield of N-vinyl-2-oxazolidone were 97.9 mole % and 88.2 mole %, respectively.

EXAMPLE 14

[Reaction]

5 ml of the catalyst of Example 10 was filled in a stainless steel-made reaction tube. Then, the reaction tube was immersed in a molten salt bath of 270° C. The inside of the reaction tube was made vacuum by the use of a vacuum pump, and N-(1-methoxyethyl)-2-oxazolidone was fed into the tube at a tube outlet pressure of 38 mmHg at a space velocity of 100 h$^{-1}$. A reaction was conducted for 50 hours continuously, after which the feeding of the raw material was stopped. The pressure inside the tube was released by introducing nitrogen thereinto. Next, air was passed through the tube for 24 hours to burn the carbonaceous substance deposited on the catalyst and regenerate the catalyst. Then, a reaction was conducted again for 50 hours continuously under the above-mentioned conditions. After 1 hour, 20 hours and 50 hours from the start of raw material feeding and after 1 hour, 20 hours and 50 hours after catalyst regeneration, the conversions of N-(1-methoxyethyl)-2-oxazolidone and the selectivities and per-pass yields of N-vinyl-2-oxazolidone are as shown in Table 1.

TABLE 1

| Time (hour) | Conversion (mole %) | Selectivity (mole %) | Per-pass yield (mole %) |
| --- | --- | --- | --- |
| After start of raw material feeding | | | |
| 1 | 99.8 | 99.2 | 99.0 |
| 20 | 99.0 | 99.6 | 98.6 |
| 50 | 98.1 | 99.8 | 97.9 |
| After catalyst regeneration | | | |
| 1 | 99.6 | 99.3 | 98.9 |
| 20 | 98.7 | 99.6 | 98.3 |
| 50 | 98.0 | 99.6 | 97.6 |

EXAMPLE 15

[Catalyst Preparation]

A solution of 6.6 g of diammonium hydrogenphosphate in 50 g of water was added to a solution of 2.1 g of lithium hydroxide monohydrate in 50 g of water. Thereto was added 30.0 g of silicon oxide. The mixture was heated with stirring, to vaporize water until the resulting residue became dry. The residue was dried in air at 120° C. for 20 hours, crushed into particles of 9–16 mesh, and calcined in air at 800° C. for 2 hours to prepare a catalyst having a composition of $P_1Li_1Si_{10}$ in terms of atomic ratio when oxygen was excluded.

[Reaction]

Using the above catalyst, a reaction was conducted in the same manner as in Example 1 except that the raw material for reaction was changed to N-(1-methoxyethyl)-O-methylcarbamate and the reaction temperature was changed to 250° C. Then, an analysis was conducted in the same manner as in Example 1. After 1 hour from the start of raw material feeding, the conversion of N-(1-methoxyethyl)-O-methylcarbamate was 93 mole %; and the selectivity and per-pass yield of N-vinyl-O-methylcarbamate were 95 mole % and 88 mole %, respectively.

COMPARATIVE EXAMPLE 2

[Reaction]

A reaction was conducted in the same manner as in Example 15 except that 5 ml of glass beads of 3 mm in diameter was filled in the reaction tube in place of the catalyst and the reaction temperature was changed to 350° C. After 1 hour from the start of raw material feeding, the conversion of N-(1-methoxyethyl)-O-methylcarbamate was 26 mole %; and the selectivity and per-pass yield of N-vinyl-O-methylcarbamate were 95 mole % and 25 mole %, respectively.

COMPARATIVE EXAMPLE 3

[Catalyst Preparation]

30.0 g of spherical silica gel of 5–10 mesh was dried in air at 120° C. for 20 hours and then calcined in air at 700° C. for 2 hours to prepare a catalyst. [Reaction]

Using the above catalyst, a reaction was conducted in the same manner as in Example 15. After 1 hour from the start of raw material feeding, the conversion of N-(1-methoxyethyl)-O-methylcarbamate was 69 mole %; and the selectivity and per-pass yield of N-vinyl-O-methylcarbamate were 98 mole % and 68 mole %, respectively.

EXAMPLE 16

[Catalyst Preparation]

A catalyst having a composition of $P_1Na_1Si_{10}$ in terms of atomic ratio when oxygen was excluded, was prepared in the same manner as in Example 15 except that lithium hydroxide monohydrate was changed to 2.0 g of sodium hydroxide and the calcination temperature was changed to 600° C.

[Reaction]

Using the above catalyst, a reaction was conducted in the same manner as in Example 15. After 1 hour from the start of raw material feeding, the conversion of N-(1-methoxyethyl)-O-methylcarbamate was 93 mole %; and the selectivity and per-pass yield of N-vinyl-O-methylcarbamate were 96 mole % and 89 mole %, respectively.

EXAMPLE 17

[Catalyst Preparation]

A catalyst having a composition of $P_1K_1Si_{10}$ in terms of atomic ratio when oxygen was excluded, was prepared in the same manner as in Example 15 except that lithium hydroxide monohydrate was changed to 2.8 g of potassium hydroxide and the calcination temperature was changed to 600° C.

[Reaction]

Using the above catalyst, a reaction was conducted in the same manner as in Example 15. After 1 hour from the start of raw material feeding, the conversion of N-(1-methoxyethyl)-O-methylcarbamate was 94 mole %; and the selectivity and per-pass yield of N-vinyl-O-methylcarbamate were 98 mole % and 92 mole %, respectively.

EXAMPLE 18

[Catalyst Preparation]

A catalyst having a composition of $P_1Rb_1Si10$ in terms of atomic ratio when oxygen was excluded, was prepared in the same manner as in Example 15 except that lithium hydroxide monohydrate was changed to 5.1 g of rubidium hydroxide and the calcination temperature was changed to 500° C.

[Reaction]

Using the above catalyst, a reaction was conducted in the same manner as in Example 15. After 1 hour from the start of raw material feeding, the conversion of N-(1-methoxyethyl)-O-methylcarbamate was 90 mole %; and the selectivity and per-pass yield of N-vinyl-O-methylcarbamate were 95 mole % and 86 mole %, respectively.

EXAMPLE 19

[Catalyst Preparation]

A catalyst having a composition of $P_1Cs_1Si_{10}$ in terms of atomic ratio when oxygen was excluded, was prepared in the same manner as in Example 15 except that lithium hydroxide monohydrate was changed to 7.5 g of cesium hydroxide and the calcination temperature was changed to 500° C.

[Reaction]

Using the above catalyst, a reaction was conducted in the same manner as in Example 15. After 1 hour from the start of raw material feeding, the conversion of N-(1-methoxyethyl)-O-methylcarbamate was 88 mole %; and the selectivity and per-pass yield of N-vinyl-O-methylcarbamate were 96 mole % and 84 mole %, respectively.

EXAMPLE 20

[Catalyst Preparation]

A solution of 13.2 g of diammonium hydrogenphosphate in 100 g of water was added to a solution of 12.6 g of lithium hydroxide monohydrate in 100 g of water. Thereto was added 30.0 g of silicon oxide. The mixture was heated with stirring, to vaporize water until the resulting residue became dry. The residue was dried in air at 120° C. for 20 hours, crushed into particles of 9–16 mesh, and calcined in air at 500° C. for 2 hours to prepare a catalyst having a composition of $P_1Li_3Si_5$ in terms of atomic ratio when oxygen was excluded.

[Reaction]

Using the above catalyst, a reaction was conducted in the same manner as in Example 15. After 1 hour from the start of raw material feeding, the conversion of N-(1-methoxyethyl)-O-methylcarbamate was 91 mole %; and the selectivity and per-pass yield of N-vinyl-O-methylcarbamate were 97 mole % and 88 mole %, respectively.

EXAMPLE 21

[Reaction]

Using the catalyst of Example 20, a reaction was conducted in the same manner as in Example 1 except that the raw material for reaction was changed to N-(1-ethoxyethyl)-O-methylcarbamate. After 1 hour from the start of raw material feeding, the conversion of N-(1-ethoxyethyl)-O-methylcarbamate was 92 mole %; and the selectivity and per-pass yield of N-vinyl-O-methylcarbamate were 97 mole % and 89 mole %, respectively.

EXAMPLE 22

[Reaction]

Using the catalyst of Example 20, a reaction was conducted in the same manner as in Example 15 except that the raw material for reaction was changed to N-(1- propoxyethyl)-O-methylcarbamate. After 1 hour from the start of raw material feeding, the conversion of N-(1-propoxyethyl)-O-methylcarbamate was 94 mole %; and the selectivity and per-pass yield of N-vinyl-O-methylcarbamate were 98 mole % and 92 mole %, respectively.

EXAMPLE 23

[Reaction]

Using the catalyst of Example 20, a reaction was conducted in the same manner as in Example 15 except that the raw material for reaction was changed to N-(1-butoxyethyl)-O-methylcarbamate. After 1 hour from the start of raw material feeding, the conversion of N-(1-butoxyethyl)-O-methylcarbamate was 95 mole %; and the selectivity and per-pass yield of N-vinyl-O-methylcarbamate were 98 mole % and 93 mole %, respectively.

EXAMPLE 24

[Catalyst Preparation]

30.0 g of silicon oxide and 8.7 g of magnesium hydroxide were suspended in 100 g of water. Thereto was added a solution of 11.5 g of a 85% aqueous phosphoric acid solution, in 100 g of water. The mixture was heated with stirring, to vaporize water until the resulting residue became dry. The residue was dried in air at 120° C. for 20 hours, crushed to particles of 9–16 mesh, and calcined in air at 500° C. for 2 hours to prepare a catalyst having a composition of $P_1Mg_{1.5}Si_5$ in terms of atomic ratio when oxygen was excluded.

[Reaction]

Using the above catalyst, a reaction was conducted for 50 hours continuously in the same manner as in Example 15. After 1 hour from the start of raw material feeding, the conversion of N-(1-methoxyethyl)-O-methylcarbamate was 93 mole %; and the selectivity and per-pass yield of N-vinyl-O-methylcarbamate were 94 mole % and 87 mole %, respectively. After 50 hours from the start of raw material feeding, the conversion of N-(1-methoxyethyl)-O-methylcarbamate was 90 mole %; and the selectivity and per-pass yield of N-vinyl-O-methylcarbamate were 96 mole % and 86 mole %, respectively.

EXAMPLE 25

[Catalyst Preparation]

A catalyst having a composition of $P_1Ba_{1.5}Si_5$ in terms of atomic ratio when oxygen was excluded, was prepared in the same manner as in Example 24 except that magnesium hydroxide was changed to 47.3 g of barium hydroxide octahydrate.

[Reaction]

Using the above catalyst, a reaction was conducted in the same manner as in Example 15 except that the reaction temperature was changed to 280° C. After 1 hour from the start of raw material feeding, the conversion of N-(1-methoxyethyl)-O-methylcarbamate was 84 mole %; and the selectivity and per-pass yield of N-vinyl-O-methylcarbamate were 95 mole % and 80 mole %, respectively.

EXAMPLE 26

[Catalyst Preparation]

30.0 g of silicon oxide was suspended in 100 of water. Thereto was added 8.6 g of calcium hydrogenphosphate dihydrate. The mixture was heated with stirring, to vaporize water until the resulting residue became dry. The residue was dried in air at 120° C. for 20 hours, crushed to particles of 9–16 mesh, and calcined in air at 500° C. for 2 hours to prepare a catalyst having a composition of $P_1Ca_1Si_{10}$ in terms of atomic ratio when oxygen was excluded.

[Reaction]

Using the above catalyst, a reaction was conducted in the same manner as in Example 15. After 1 hour from the start of raw material feeding, the conversion of N-(1-methoxyethyl)-O-methylcarbamate was 94 mole %; and the selectivity and per-pass yield of N-vinyl-O-methylcarbamate were 98 mole % and 92 mole %, respectively.

EXAMPLE 27

[Catalyst Preparation]

30 g of tricalcium phosphate and 20 g of water were kneaded in a mortar. The mixture was dried in air at 120° C. for 20 hours, crushed to particles of 9–16 mesh, and calcined in air at 500° C. for 2 hours to prepare a catalyst having a composition of $P_1Ca_{1.5}$ in terms of atomic ratio when oxygen was excluded.

[Reaction]

Using the above catalyst, a reaction was conducted in the same manner as in Example 15. After 1 hour from the start of raw material feeding, the conversion of N-(1-methoxyethyl)-O-methylcarbamate was 96 mole %; and the selectivity and per-pass yield of N-vinyl-O-methylcarbamate were 92 mole % and 88 mole %, respectively.

EXAMPLE 28

[Reaction]

Using the catalyst of Example 26, a reaction was conducted in the same manner as in Example 15 except that the raw material for reaction was changed to N-(1-methoxyethyl)-N-methyl-O-methylcarbamate. After 1 hour from the start of raw material feeding, the conversion of N-(1-methoxyethyl)-N-methyl-O-methylcarbamate was 96 mole %; and the selectivity and per-pass yield of N-vinyl-N-methyl-O-methylcarbamate were 95 mole % and 91 mole %, respectively.

EXAMPLE 29

[Reaction]

Using the catalyst of Example 26, a reaction was conducted in the same manner as in Example 15 except that the raw material for reaction was changed to N-(1-methoxyethyl)-N-ethyl-O-methylcarbamate. After 1 hour from the start of raw material feeding, the conversion of N-(1-methoxyethyl)-N-ethyl-O-methylcarbamate was 95 mole %; and the selectivity and per-pass yield of N-vinyl-N-ethyl-O-methylcarbamate were 93 mole % and 88 mole %, respectively.

EXAMPLE 30

[Reaction]

Using the catalyst of Example 4, a reaction was conducted in the same manner as in Example 15 except that the raw material for reaction was changed to N-(1-methoxypropyl)-O-methylcarbamate. After 1 hour from the start of raw material feeding, the conversion of N-(1-methoxypropyl)-O-methylcarbamate was 94 mole %; and the selectivity and per-pass yield of N-(1-propenyl)-O-methylcarbamate were 93 mole % and 87 mole %, respectively.

EXAMPLE 31

[Reaction]

Using the catalyst of Example 6, a reaction was conducted in the same manner as in Example 15 except that the raw material for reaction was changed to N-(1-methoxybutyl)-O-methylcarbamate. After 1 hour from the start of raw material feeding, the conversion of N-(1-methoxybutyl)-O-methylcarbamate was 89 mole %; and the selectivity and per-pass yield of N-(1-butenyl)-O-methylcarbamate were 96 mole % and 85 mole %, respectively.

EXAMPLE 32

[Reaction]

Using the catalyst of Example 5, a reaction was conducted in the same manner as in Example 15. After 1 hour from the start of raw material feeding, the conversion of N-(1-methoxyethyl)-O-methylcarbamate was 94 mole %; and the selectivity and per-pass yield of N-vinyl-O-methylcarbamate were 94 mole % and 88 mole %, respectively.

EXAMPLE 33

[Catalyst Preparation]

A solution of 57.6 g of a 85% aqueous phosphoric acid solution, in 200 g of water was added to a suspension of 21.0 g of lithium hydroxide monohydrate and 14.5 g of magnesium hydroxide in 200 g of water. The mixture was heated with stirring, to vaporize water until the resulting residue became dry. The residue was dried in air at 120° C. for 20 hours, crushed into particles of 9–16 mesh, and calcined in air at 500° C.; for 2 hours to prepare a catalyst having a composition of $P_1Li_1Mg_{0.5}$ in terms of atomic ratio when oxygen was excluded.

[Reaction]

Using the above catalyst, a reaction was conducted in the same manner as in Example 15 except that the reaction temperature was changed to 260° C. After 1 hour from the start of raw material feeding, the conversion of N-(1-methoxyethyl)-O-methylcarbamate was 90 mole %; and the selectivity and per-pass yield of N-vinyl-O-methylcarbamate were 97 mole % and 87 mole %, respectively.

EXAMPLE 34

[Catalyst Preparation]

30.0 g of silicon oxide was added to a solution of 5.8 g of a 85% aqueous phosphoric acid solution, in 100 g of water. Thereto was added a solution of 2.6 g of lithium hydroxide monohydrate in 50 g of water. The mixture was heated with stirring, to vaporize water until the resulting residue became dry. The residue was dried in air at 120° C. for 20 hours, crushed into particles of 9–16 mesh, and calcined in air at 700° C. for 2 hours to prepare a catalyst having a composition of $P_1Li_{1.25}Si_{10}$ in terms of atomic ratio when oxygen was excluded.

[Reaction]

5 ml of the above catalyst was filled in a stainless steel-made reaction tube. Then, the reaction tube was immersed in a molten salt bath of 250° C. The inside of the reaction tube was made vacuum by the use of a vacuum pump, and N-(1-methoxyethyl)-O-methylcarbamate was fed into the tube at a tube outlet pressure of 76 mmHg at a space velocity of 200 h$^{-1}$. A reaction was conducted for 50 hours continuously, after which the feeding of the raw material was stopped. The pressure inside the tube was released by introducing nitrogen thereinto. Next, air was passed through the tube for 24 hours to burn the carbonaceous substance deposited on the catalyst and regenerate the catalyst. Then, a reaction was conducted again for 50 hours continuously under the above-mentioned conditions. After 1 hour and 50 hours from the start of raw material feeding and after 1 hour and 50 hours after catalyst regeneration, the conversions of N-(1-methoxyethyl)-O-methylcarbamate and the selectivities and per-pass yields of N-vinyl-O-methylcarbamate are as shown in Table 2.

TABLE 2

| Time (hour) | Conversion (mole %) | Selectivity (mole %) | Per-pass yield (mole %) |
|---|---|---|---|
| After start of raw material feeding | | | |
| 1 | 94 | 96 | 90 |
| 50 | 92 | 98 | 90 |
| After catalyst regeneration | | | |
| 1 | 94 | 97 | 91 |
| 50 | 91 | 98 | 89 |

EXAMPLE 35

[Reaction]

Using the catalyst of Example 34, a reaction was conducted in the same manner as in Example 1 except that the raw material for reaction was changed to N-(1-isopropoxyethyl)acetamide and the reaction temperature was changed to 200° C. After 1 hour from the start of Taw material feeding, the conversion of N-(1-isopropoxyethyl) acetamide was 94.5 mole %; and the selectivity and per-pass yield of N-vinylacetamide were 100 mole % and 94.5 mole %, respectively.

EXAMPLE 36

[Reaction]

Using the catalyst of Example 34, a reaction was conducted in the same manner as in Example 1 except that the raw material for reaction was changed to N-(1-ethoxyethyl)-2-pyrrolidone and the reaction temperature was changed to 220° C. After 1 hour from the start of raw material feeding, the conversion of N-(1-ethoxyethyl)-2-pyrrolidone was 93.0 mole %; and the selectivity and per-pass yield of N-vinylpyrrolidone were 100 mole % and 93.0 mole %, respectively.

EXAMPLE 37

[Reaction]

Using the catalyst of Example 34, a reaction was conducted in the same manner as in Example 1 except that the raw material for reaction was changed to N-(1-ethoxyethyl)

-N-methylacetamide and the reaction temperature was changed to 200° C. After 1 hour from the start of raw material feeding, the conversion of N-(1-ethoxyethyl)-N-methylacetamide was 98.7 mole %; and the selectivity and per-pass yield of N-vinyl-N-methylacetamide were 100 mole % and 98.7 mole %, respectively.

What is claimed is:

1. A process for producing an N-vinyl compound of the following formula (2)

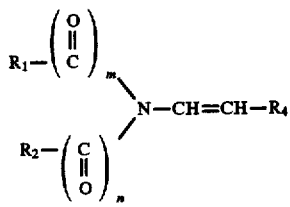
(2)

wherein m and n are each independently 0 or 1, $R_1$ and $R_2$ are each independently one member selected from the group consisting of hydrogen, hydrocarbon groups having 1–8 carbon atoms and alkoxy groups having 1–6 carbon atoms, with the provisos that (i) when m and n are each 0, none of $R_1$ and $R_2$ are hydrogen, and (ii) when none of $R_1$ and $R_2$ are hydrogen, $R_1$ and $R_2$ may bond to each other to form, together with N, a five- to seven-membered ring which may contain unsaturated bond(s) and/or hetero atom(s) selected from the group consisting of S, O and N other than said N already shown in formula (2), and $R_4$ is one member selected from the group consisting of hydrogen and hydrocarbon groups having 1–6 carbon atoms, said process comprising:

subjecting an N-(1-alkoxyalkyl) compound of the following formula (1)

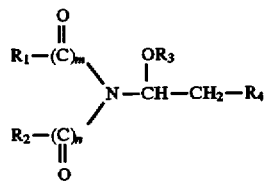
(1)

wherein $R_1$, $R_2$, $R_4$, m and n are the same as in formula (2), and $R_3$ is one member selected from the group consisting of methyl group, ethyl group, propyl group and butyl group, to alcohol elimination in a gas phase in the presence of a solid oxide catalyst of the following formula (13)

PaXbYcOd (13)

wherein

P is phosphorus,

X is at least one element selected from the group consisting of alkali metals and alkaline earth metals, Y is at least one element selected from the group consisting of Ti, Zr, Nb, B, Al and Si, O is oxygen, a, b, c and d are the atomic ratios of P, X, Y and O, respectively, with a:b:c being 1:0.5–5:0–500, and d being determined by a, b, c and the bonding states of the individual elements to convert said N-(1-alkoxyalkyl) compound of the formula (1) into an N-vinyl compound of the formula (2).

2. The process according to claim 1, wherein said N-(1-alkoxyalkyl) compound is an N-(1-alkoxyalkyl)-2-oxazolidone of the following formula (3)

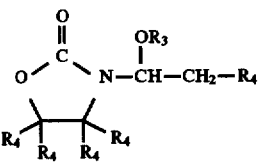
(3)

wherein $R_3$ is one member selected from the group consisting of methyl group, ethyl group, propyl group and butyl group, and $R_4$ is one member selected from the group consisting of hydrogen, methyl group and ethyl group, and said N-(1-alkoxyalkyl)-2-oxazolidone of the formula (3) is subjected to said alcohol elimination to produce an N-vinyl-2-oxazolidone of the following formula (4)

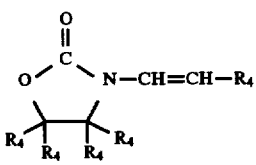
(4)

wherein $R_4$ is the same as in formula (3).

3. The process according to claim 1, wherein said N-(1-alkoxyalkyl) compound is an N-(1-alkoxyalkyl)-O-alkylcarbamate of the following formula (5)

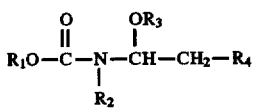
(5)

wherein $R_1$ and $R_3$ are each independently one member selected from the group consisting of methyl group, ethyl group, propyl group and butyl group, $R_2$ is one member selected from the group consisting of hydrogen and hydrogen groups having 1–4 carbon atoms, and $R_4$ is one member selected from the group consisting of hydrogen, methyl group and ethyl group, and said N-(1-alkoxyalkyl)-O-alkylcarbamate of the formula (5) is subjected to said alcohol elimination to produce an N-vinyl-O-alkylcarbamate of the following formula (6)

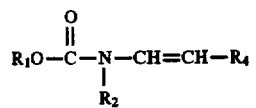
(6)

wherein $R_1$, $R_2$ and $R_4$ are the same as in formula (5).

4. The process according to claim 1, wherein said N-(1-alkoxyalkyl) compound is an N-(1-alkoxyalkyl)-amide of the following formula (7)

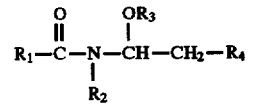
(7)

wherein $R_1$ and $R_2$ are each independently one member selected from the group consisting of hydrogen and hydrocarbon groups having 1–8 carbon atoms with the proviso that $R_1$ and $R_2$ may bond to each other to form, together with N, a five- to seven-membered ring which may contain hetero atom(s) selected from the group consisting of S, O and N other than said N, $R_3$ is one member selected from the group consisting of methyl group, ethyl group, propyl group and butyl group, and $R_4$ is one member selected from the group consisting of hydrogen and hydrocarbon groups having 1–6 carbon atoms, and said N-(1-alkoxyalkyl)-amide of the formula (7) is subjected to said alcohol elimination to produce an N-vinylamide of the following formula (8)

wherein $R_1$, $R_2$ and $R_4$ are the same as in formula (7).

* * * * *